US009642829B2

(12) United States Patent
Seneviratne et al.

(10) Patent No.: US 9,642,829 B2
(45) Date of Patent: May 9, 2017

(54) ANTIFUNGAL COMPOUND AND USES THEREOF

(71) Applicant: The University of Hong Kong, Hong Kong (CN)

(72) Inventors: Chaminda Jayampath Seneviratne, Hong Kong (CN); Yi Tsun Richard Kao, Hong Kong (CN); Lakshman Perera Samaranayake, Hong Kong (CN); Kwok Yung Yuen, Hong Kong (CN); Dan Yang, Hong Kong (CN); Yu Wang, Hong Kong (CN); Sze Wah Sarah Wong, Hong Kong (CN)

(73) Assignee: THE UNIVERSITY OF HONG KONG, Hong Kong (CN)

(*) Notice: Subject to any disclaimer, the term of this patent is extended or adjusted under 35 U.S.C. 154(b) by 0 days.

(21) Appl. No.: 14/095,757

(22) Filed: Dec. 3, 2013

(65) Prior Publication Data
US 2014/0155478 A1    Jun. 5, 2014

Related U.S. Application Data

(60) Provisional application No. 61/733,094, filed on Dec. 4, 2012.

(51) Int. Cl.
*C07D 309/34* (2006.01)
*A61K 31/351* (2006.01)
(Continued)

(52) U.S. Cl.
CPC ............ *A61K 31/351* (2013.01); *A01N 43/40* (2013.01); *A01N 59/00* (2013.01); *A61K 9/0019* (2013.01); *A61K 9/08* (2013.01)

(58) Field of Classification Search
None
See application file for complete search history.

(56) References Cited

U.S. PATENT DOCUMENTS 7,825,143 B2    11/2010   Toenjes et al.
2004/0106663 A1   6/2004   Talley et al.
(Continued)

OTHER PUBLICATIONS

Ericksen, Antibacterial Activity and Specificity of the Six Human α-Defensins, Antimicrobial Agents and Chemotherapy, 2005, pp. 269-275.*

(Continued)

*Primary Examiner* — San-Ming Hui
*Assistant Examiner* — Andrew Lee
(74) *Attorney, Agent, or Firm* — Leason Ellis LLP

(57) ABSTRACT

Disclosed herein is a novel antifungal compound, derivatives that are used to treat fungal infections. In a specific embodiment, the compound is a small molecule. In a specific embodiment, the compound described herein inhibits yeast to hypha transition under robust hyphal inducing conditions at lower concentration of the molecule. Also disclosed is a composition comprising the antifungal compound. In a specific embodiment, the composition is a pharmaceutical composition. Also disclosed is a method of treating and/or preventing fungal infection using the disclosed compound. The disclosed compound exhibits antifungal activity against wide range of fungal species at slightly higher concentrations. Antifungal compound disclosed herein is used as anti-biofilm agent against fungal infections.

22 Claims, 8 Drawing Sheets

Figure 1:
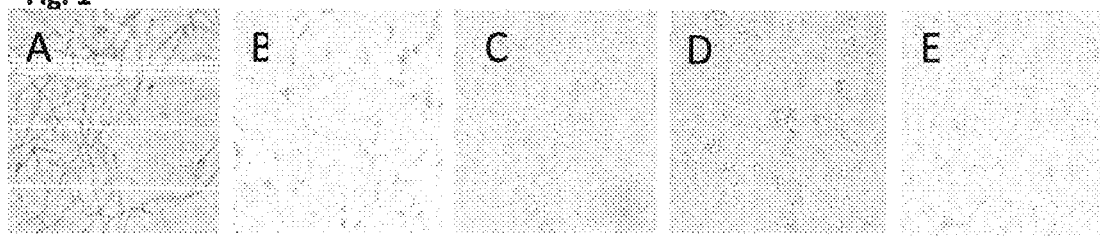
Figure 1:
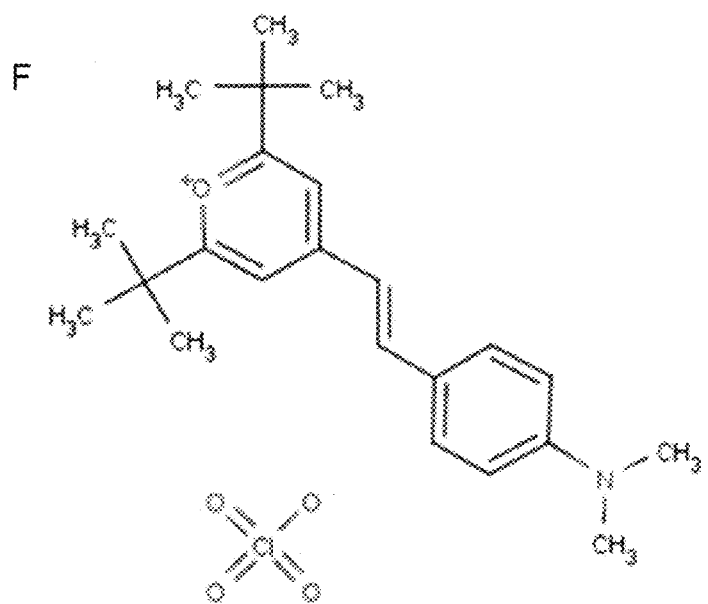

(51) Int. Cl.
  *A01N 43/40* (2006.01)
  *A01N 59/00* (2006.01)
  *A61K 9/00* (2006.01)
  *A61K 9/08* (2006.01)

(56) References Cited

U.S. PATENT DOCUMENTS

2006/0154991 A1 7/2006 Johnson et al.
2006/0194769 A1 8/2006 Johnson et al.

OTHER PUBLICATIONS

Thevissen, Specific Binding Sites for an Antifungal Plant Defensin from Dahlia (Dahlia merckii) on Fungal Cells are Required for Antifungal Activity, MPMI, 2000, 13(1), pp. 54-61.*

Calugi, et al. "Novel small molecules for the treatment of infections caused by Candida albicans: a patent review" (2002-2010), *Expert Opin Ther Pat.* 2011, vol. 21(3), pp. 381-397.

LaFleur MD, et al., "Novel high-throughput screen against Candida albicans identifies antifungal potentiators and agents effective against biofilms", *J Antimicrob Chemother.* 2011, vol. 66(4), pp. 820-826.

Trabocchi, et al., "Identification of inhibitors of drug-resistant Candida albicans strains from a library of bicyclic peptidomimetic compounds", *J Med Chem.* 2010, vol. 53(6), pp. 2502-2509.

Toenjes, et al., Inhibitors of cellular signalling are cytotoxic or block the budded-to-hyphal transition in the pathogenic yeast Candida albicans, *J Med Microbiol.* 2009, vol. 58, pp. 779-790.

Kitamura, et al., "In vitro antifungal activities of D11-2040, a beta-1,6-glucan inhibitor, with or without currently available antifungal drugs," *Biol Pharm Bull.* 2010, vol. 33(2), pp. 192-197.

Fera, et al., "New triazoles and echinocandins: mode of action, in vitro activity and mechanisms of resistance," *Expert Rev Anti Infect Ther.* 2009, vol. 7(8), pp. 981-998.

F. Sabatelli, R. Patel, et al., "In Vitro Activities of Posaconazole, Fluconazole, Itraconazole, Voriconazole, and Amphotericin B against a Large Collection of Clinically Important Molds and Yeasts," *Antimicrobial Agents and Chemotherapy,* Jun. 2006, vol. 50, No. 6, pp. 2009-2015.

* cited by examiner

ANTIFUNGAL COMPOUND AND USES THEREOF

RELATED APPLICATIONS

This application claims the benefit of U.S. provisional application Ser. No. 61/733,094, filed Dec. 4, 2012, which is hereby incorporated by reference in its entirety.

1. INTRODUCTION

Disclosed herein is a novel compound and derivatives thereof that are used to treat fungal infections. Also disclosed is a composition comprising the compound. In certain embodiments, the composition is a pharmaceutical composition. In certain embodiments, the composition is a paint composition. Also disclosed is a method of reducing fungal growth and a method of treating and/or preventing fungal infection using the disclosed compound. The disclosed compound exhibits antifungal activity against a wide range of fungal species. The compound disclosed herein is used as anti-biofilm agent against bacterial and fungal infections. In certain embodiments, the disclosed compound is effective for systemic fungal infections. In certain embodiments, the disclosed compound is a broad-spectrum antifungal agent for treating topical, local and/or systemic fungal infections. In certain embodiments, the disclosed compound is used in the prevention or treatment of mycotic infections caused by various fungal pathogens. Provided herein is a medical device comprising a coating comprising the compound disclosed herein. Provided herein is a method of making a medical device comprising a coating comprising the compound disclosed herein. Provided herein is a method of making an anti-biofilm surface. Also provided herein is a paint composition comprising the compound disclosed herein.

2. BACKGROUND

Fungal infections are a huge clinical burden and highly prevalent among compromised host populations worldwide. Fungal pathogens in humans cause both superficial mucosal and systemic mycoses with higher morbidity and mortality rates. For instance, recent studies including ours, indicated that mortality rate of systemic candidiasis among hospitalized patients could be as high as 70% under compromised conditions. Treatment for fungal infections, including hospital stay, is costly.

During last couple of years fungal infection has become a major threat to hospitalized patients worldwide. In particular, *Candida* is the major fungal pathogen in humans which cause millions of mucosal and systemic mycoses worldwide. Despite the currently available antifungal agents, *Candida* remains to be the ubiquitous pathogen causing severe mucosal infections such as oral candidiasis, onycomycoses (nails), vulvovaginal candidiasis as well as systemic mycoses. Hence, candidiasis is a leading cause of hospital-acquired infection, surpassing most bacterial infections. Unlike most bacterial diseases, fungal diseases are difficult to treat. Hence, there is higher mortality associated with systemic candidiasis. Local data from Hong Kong indicate mortality of systemic candidiasis in hospital settings could be as high as 70%. Rising drug resistance for available drug as indicated global surveys is a major problem for treating fungal infections. Development of more effective antifungal drugs with lesser side effects has become a highest priority in the field. Therefore, novel antifungal compounds with such desirable properties will be of great clinical importance. Compromised host populations such as HIV/AIDS patients, organ transplant recipients, patients on chemotherapy are expected to rise over next decade and those groups are highly prone to fungal infections with serious consequences. Therefore, there is an increasing demand for antifungal agents that have excellent inherent pharmacokinetic characteristics and potent inhibitory activities against a broad spectrum of fungi. Although there are several classes of antifungal agents are currently available, none of them, however, are sufficiently satisfactory for use as medicine in that they do not exhibit all of excellent inhibitory activity against some of the opportunistic fungi which cause fatal infections and suitable pharmacokinetics within the body.

The fungal pathogen *Candida* species are common causes of opportunistic and systematic infection, which may be lethal in immunodeficient individuals including those HIV-infected and radio- or chemo-therapy recipients. *Candida albicans* is the most prevalent *Candida* species isolated from human hosts. It lives as a commensal in skin, oral cavity and esophagus, gastrointestinal tract, vagina and vascular system and causes disease when given the opportunity. *Candida albicans* is able to switch between the yeast and the hyphal form, thus combining the better dispersal properties of the yeast form with the invasive properties of the hyphal form. The hyphae can penetrate the epithelium into the host cell to acquire nutrients for fungi, resulting in invading or damaging these tissues or organs. The reversible morphological transitions into hyphal growth forms can further enhance *C. albicans*' virulence.

Usually *Candida* spp. resides in a mixed habitation with other microbial. Such habitation is biofilm. In biofilms, the inhabitants (mainly fungi and bacteria) are encapsulated into a matrix of glycoproteins and polysaccharides produced by themselves and they usually reside with low metabolic activity. Through biofilm, *Candida* can adhere to denture, implanted medical device (including catheter and heart valves) and tissue surfaces, denture and host organs with strong resistance to anti-fungal treatment. This makes the *Candida* infection hard to treat. On the other hand, the various virulent inhabitants within the biofilm are more harmful than single *Candida* population. As a result, an implanted device is always associated these infections and a biofilm can be detected on the surface of the device. *Candida* spp. becomes common pathogen and is regarded as agents of nosocomial pneumonias and urinary tract infections, without effective treatment. Despite increasing numbers of health-compromised people, who are prone to contracting life-threatening fungal diseases, only a few classes of anti-fungal drugs, such as polyenes, azoles, echinocandins, allylamines, and flucytosine, are available for the treatment of fungal infections.

However, polyenes have dose-related toxicity, particularly nephrotoxicity, although the introduction of lipid formulations has improved risk-benefit ratio. In addition, rising drug resistance is an inevitable problem. Emergence of drug-resistant strains to fluconazole, a drug of choice for AIDS patient has become a major problem, although second-generation triazoles have addressed some issues (Fera M T, La Camera E, De Sarro A. New triazoles and echinocandins: mode of action, in vitro activity and mechanisms of resistance. Expert Rev Anti Infect Ther. 2009; 7(8):981-98. Therapeutic failures and emergence of resistance have already been reported for recently introduced echinocandin antifungal agents. As a result of the limitations of existing antifungal agents, mortality rates for candidemia remain high. This situation highlights the urgent need for more effective and safer antifungal agents for this ubiquitous fungal infection, for example, recalcitrant *Candida* infection.

3. SUMMARY

Provided herein is a compound having the structure in FIG. 1F, derivatives thereof; or a pharmaceutically acceptable salt, solvate, or hydrate thereof. In one embodiment, the compound is SM21. SM21 showed a better antifungal activity against resistant fungal isolates for presently available antifungal agents. Moreover, the compound described herein also exhibited potent anti-biofilm activity against fungal biofilms that are resistant to currently available antifungal agents. In certain embodiments, SM21 is an antifungal agent against a broad spectrum of fungal infections. Also described herein is a composition comprising the compound. In certain embodiments, the composition is a pharmaceutical composition that includes solutions, suspensions, gels, fluid gels, emulsions, emulsion gels, lotions, ointments, film forming solutions, creams, sprays and lacquers. In particular, the antifungal composition is used to treat or prevent local or systemic fungal infection in a subject. In specific embodiment, the subject is a mammal. In specific embodiment, the subject is human. In one embodiment, provided herein is a method of treating fungal infection comprising administering to a subject, a pharmaceutical formulation comprising a therapeutically effective amount of one or more antifungal agents.

Provided herein is a method for reducing growth of a fungus comprising contacting a fungal cell with a compound having a structure:

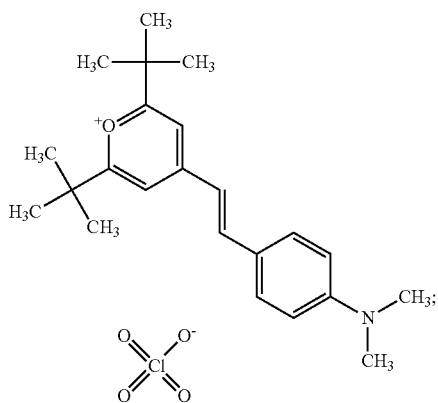 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier.

In certain embodiments, the fungal cell is a pathogenic yeast. In certain embodiments, the fungal cell is *Candida albicans, Pneumocystis carinii, Saccharomyces cerevisiae, Aspergillus nidulans, Kluyveromyces lactis, Schizosaccharomyces pombe, Streptomyces lasaliensis, Streptomyces hygroscopicus, Candida tropicalis, Candida dubliniensis, Candida parapsilosis, Candida kefyr, Candida guilliermondii, Candida inconspicua, Candida famata, Candida glabrata, Candida krusei, Candida lusitaniae, Cryptococcus neoformans, Coccidioides immitis, Hispolasma capsulatum* or a combination thereof.

Provided herein is a method of treating and preventing against fungal infections in a subject which comprises administering to the subject an effective amount of a compound having the structure:

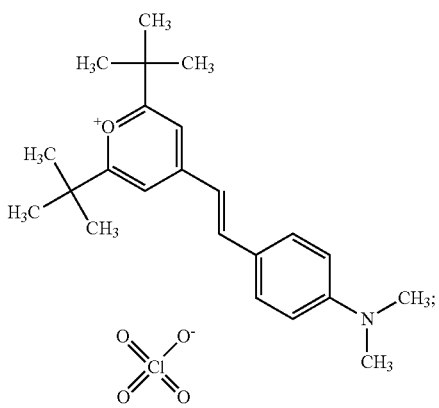 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier.

In certain embodiments, the subject is a human. In certain embodiments, the subject is immunocompromised. In certain embodiments, the subject had received chemotherapy. In certain embodiments, the subject has AIDS. In certain embodiments, the subject had received a transplant. In certain embodiments, the subject has a central venous catheter. In certain embodiments, the compound is administered via injection, topical route, oral route, nasal route, aerosol, or enema route.

Also provided herein is a medical device having a surface wherein at least a portion of the surface comprises a coating wherein the coating comprises a compound having a structure:

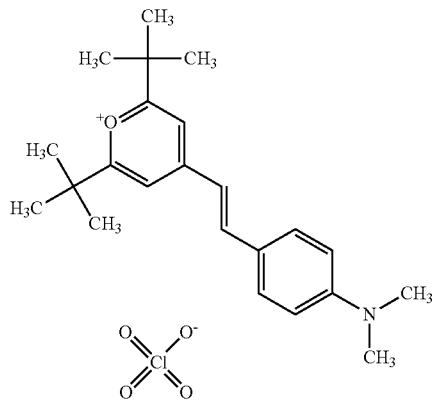 [SMILES: CN(C)c1ccc(/C=C/c2cc(C(C)(C)C)[o+]c(C(C)(C)C)c2)cc1 ; [O-][Cl+3]([O-])([O-])[O-]]

Also provided herein is a method of making a medical device of claim 14 comprising the steps of:
(a) providing a medical device having a surface; and
(b) applying a coating composition comprising a compound having a structure:

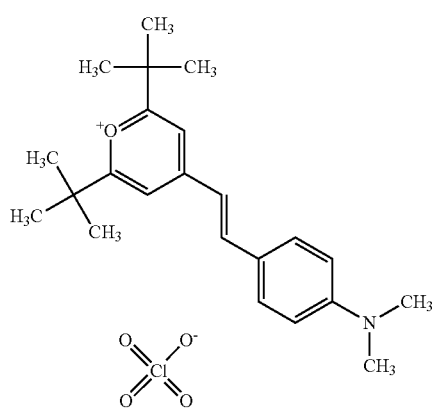 [SMILES: CN(C)c1ccc(/C=C/c2cc(C(C)(C)C)[o+]c(C(C)(C)C)c2)cc1 ; [O-][Cl+3]([O-])([O-])[O-]]

to at least a portion of the surface.

4. DESCRIPTION OF THE FIGURES

FIGS. 1A-F: Yeast-to-hypha inhibitory properties of SM21 under strong hyphal inducing conditions. Several environmental conditions which are known to induce the hyphal formation of *C. albicans* such as serum, Lee's medium, Spider medium, temperature and 37° C. were used to test the ability of SM21 to inhibit Y—H transition. (A) Control samples showing *C. albicans* hyphal formation (B) Test samples were incubated with SM21 at Y-Hi concentration showing yeast morphology (C-E) *C. albicans* clinical strains A15 (C), H2 (D) and H11 (E) incubated with SM21 at Y-Hi concentration for 24 h. SM21 could act as a Y-Hi at a lower concentration of 0.025 µg/ml and 0.0.5 µg/ml for $10^4$ cells/ml and $10^6$ cells/ml of *C. albicans*, respectively. Chemical structure of SM21 is shown in (F).

Figure 2:
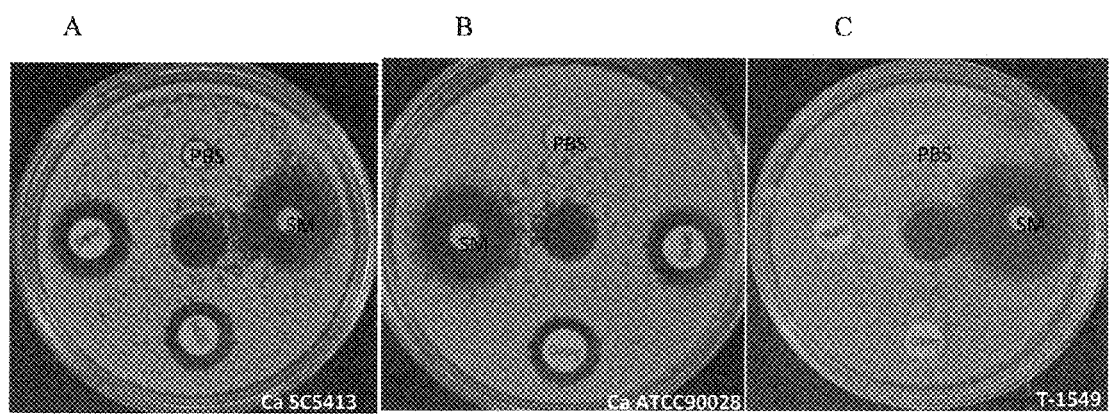

FIGS. 2A-C: (A) *C. albicans* SC5314 and (B) *C. albicans* ATCC 90028 (CLSI quality control strain) and (C) resistant isolate T-1549 were used to determine the antifungal activity of SM21 comparing for those of caspofungin and amphotericin B. *C. albicans* SC5314 and *C. albicans* ATCC 90028 were susceptible to all three agents, but only SM21 was effective for resistant isolate.

FIGS. 3A-C. Antibacterial activity of SM21 at dose of 2 µg was examined for three bacterial species together with other antifungal agents caspofungin, amphotericin B and chlorhexidine. (A) *Lactobacillus acidophilus* (B) *Streptococcus mutans* and (C) *Escherichia coli* were used for the experiments. SM21 was not anti-bacterial at the concentration effective for fungal species demonstrating its fungal-specific activity akin to other antifungal agents.

Figure 4:
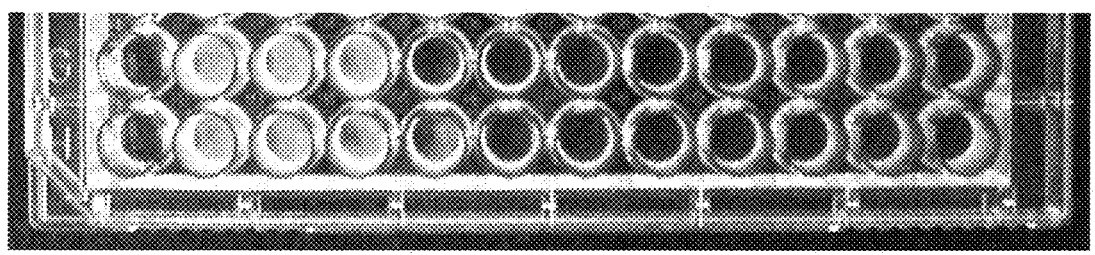
Figure 4:
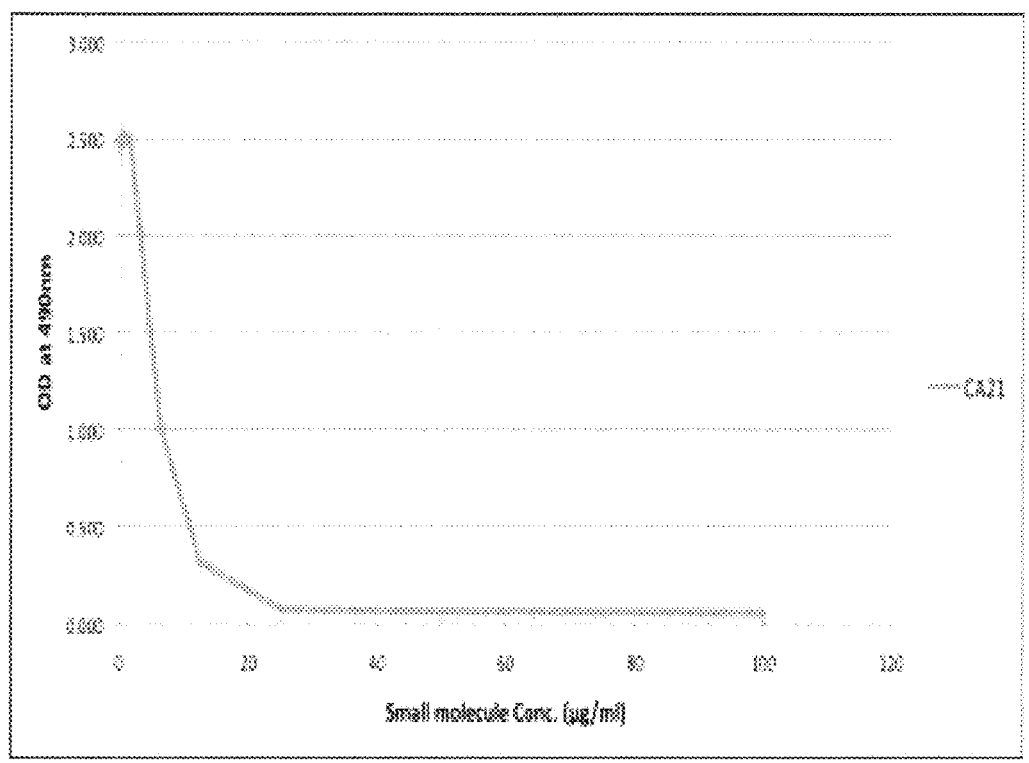

FIGS. 4A-B. Minimum effective anti-biofilm concentration for 24 h *C. albicans* biofilms. (A) Concentration of compound used. (B) Graph for minimum effective anti-biofilm concentration.

Figure 5:
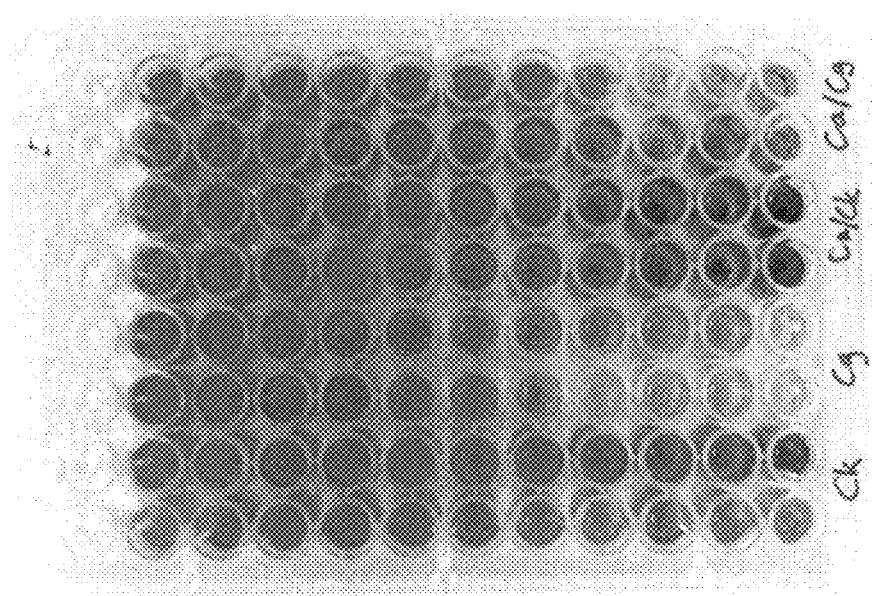

FIG. 5. XTT reduction assay for *Candida* biofilms showing effect of SM21

Figure 6:
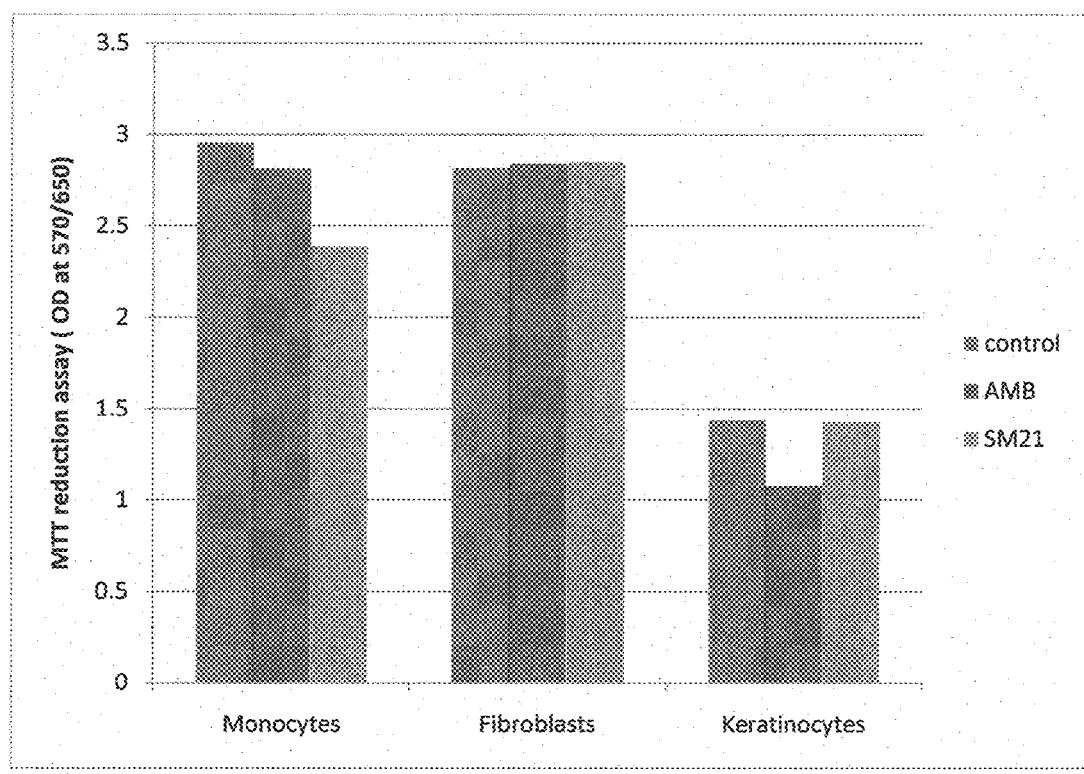

FIG. 6. MTT reduction assay of primary culture human monocytes, gingival fibroblasts and oral keratinocytes showing safety of SM21.

Figure 7:
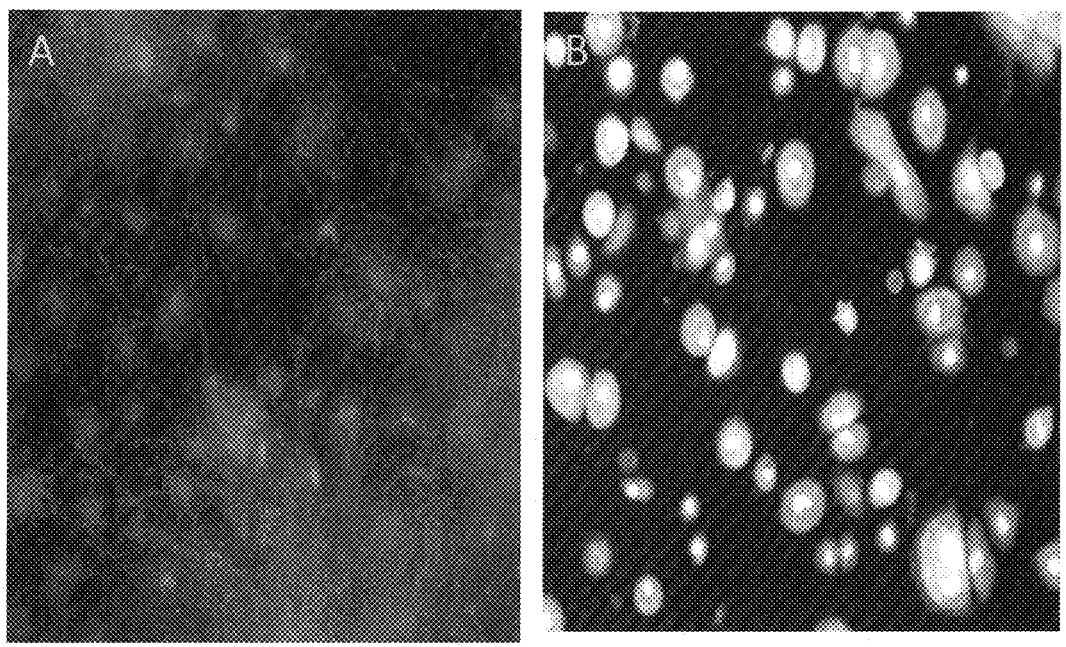

FIGS. 7A-B. SM21 is able to effectively inhibit the *Candida* invasion of epithelial cells in *Candida*-HOK co-culture model. (A) Control samples showing *Candida* hyphae and dead keratinocytes. (B) samples treated with SM21 showing live keratinocytes.

Figure 8:
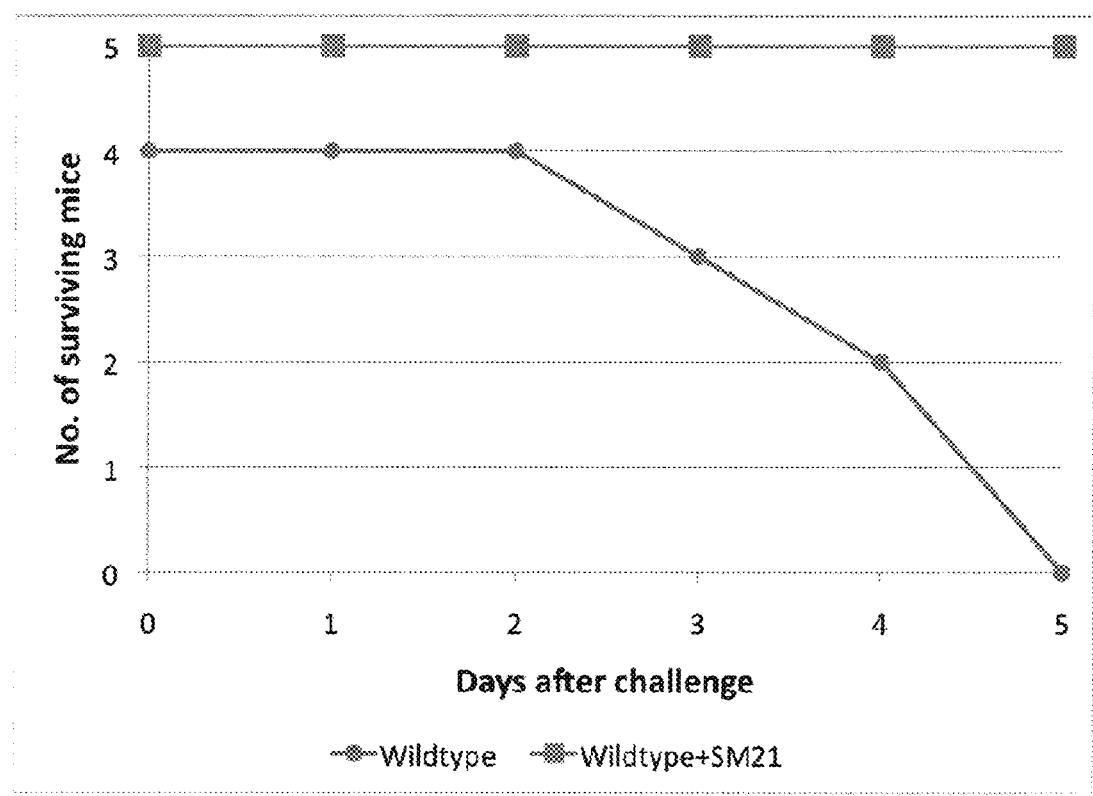

FIG. 8. SM21 effectively saved all the mice from systemic candidiasis

4.1 DEFINITIONS

When referring to the compounds provided herein, the following terms have the following meanings unless indicated otherwise.

"Pharmaceutically acceptable salt" includes any salt of a compound provided herein which retains its biological properties and which is not toxic or otherwise undesirable for pharmaceutical use. Such salts may be derived from a variety of organic and inorganic counter-ions well known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "Solvate" includes a compound provided herein or a salt thereof, that further includes a stoichiometric or non-stoichiometric amount of solvent bound by non-covalent intermolecular forces. Where the solvent is water, the solvate is a hydrate.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In one embodiment, the subject is refractory or non-responsive to current treatments for hepatitis C infection. In another embodiment, the subject is a farm animal (e.g., a horse, a cow, a pig, etc.) or a pet (e.g., a dog or a cat). In one embodiment, the subject is a human.

As used herein subject in need thereof is a subject having a fungal infection, or a subject at risk of developing a fungal infection. The subject may have been diagnosed as having such a fungal infection as described herein or using standard medical techniques known to those of skill in the art. Alternatively a subject may exhibit one or more symptoms of fungal infection.

A subject at risk of developing a fungal infection is a subject who has been exposed to a fungus, or is susceptible to exposure to a fungus. For instance a subject that is susceptible to exposure to a fungus includes those subjects who work with fungal material or in areas of high fungal content, subjects who travel to areas with high fungal infectivity rates or are otherwise likely to be exposed to a fungal infection as well as those subjects having particular susceptibility to fungal infection resulting from medical conditions or therapies. Examples of subjects having particular susceptibility to fungal infections arising from medical conditions or therapies include but are not limited to an immunocompromised subject, a subject having received chemotherapy, a subject having cancer, a subject having AIDS, a subject who is HIV positive, a subject who is at risk of being HIV positive, a subject having received a transplant, or a subject having a central venous catheter.

An immunocompromised subject is a subject that is incapable of inducing a normal effective immune response or a subject that has not yet developed an immune system (e.g. preterm neonate). An immunocompromised subject, for example, is a subject undergoing or undergone chemotherapy, a subject having AIDS, a subject receiving or having received a transplant or other surgical procedure etc.

A subject having received chemotherapy is a subject that has undergone some form of chemotherapeutic procedure. Chemotherapeutic procedure encompasses conventional methods known to those of skill in the art. Examples of chemotherapeutic methods include but are not limited to alkylating agents, for example, nitrogen mustards, ethyleneimine compounds and alkyl sulphonates; antimetabolites, for example, folic acid, purine or pyrimidine antagonists, mitotic inhibitors, for example, vinca alkaloids and derivatives of podophyllotoxin; cytotoxic antibiotics; compounds that damage or interfere with DNA expression; and growth factor receptor antagonists; antibodies and other biological molecules known to those of ordinary skill in the art.

A subject who is HIV positive encompasses a subject who is a carrier of any of the HIV family of retroviruses or a subject who is diagnosed of active AIDS, as well as a subject having AIDS-related conditions. A carrier of HIV may be identified by any methods known in the art. For example, a subject can be identified as an HIV carrier on the basis that the subject is anti-HIV antibody positive, or is HIV-positive, or has symptoms of AIDS. HIV infection generally encompasses infection of a host, particularly a human host, by the human immunodeficiency virus (HIV) family of retroviruses including, but not limited to, HIV I, HIV II, HIV III (also known as HTLV-II, LAV-1, LAV-2), and the like. "HIV" can be used herein to refer to any strains, forms, subtypes and variations in the HIV family. A subject having HIV is a subject who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4+ T cells), and AIDS (which is defined by more serious AIDS-defining illnesses and/or a decline in the circulating CD4 cell count to below a level that is compatible with effective immune function). In addition, it is intended to encompass subjects suspected of being infected with HIV after suspected past exposure to HIV by e.g., contact with HIV-contaminated blood, blood transfusion, exchange of body fluids, "unsafe" sex with an infected subject, accidental needle stick, receiving a tattoo or acupuncture with contaminated instruments, or transmission of the virus from a mother to a baby during pregnancy, delivery or shortly thereafter. Subjects who are HIV positive also encompass subjects who have not been diagnosed as having HIV infection but are believed to be at high risk of infection by HIV.

A subject having acquired immunodeficiency syndrome (AIDS) is a subject who exhibits more serious AIDS-defining illnesses and/or a decline in the circulating CD4 cell count to below a level that is compatible with effective immune function. A subject having AIDS also encompasses a subject having AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, Mycobacterial tuberculosis, esophageal candidiasis, toxoplasmosis of the brain, CMV retinitis, HIV-related encephalopathy, HIV-related wasting syndrome, etc.

A subject having received a transplant is a subject having received either a tissue or organ transplant during a surgical procedure. Transplants include but are not limited to organ, tissue, stem cell, bone marrow, and encompass conventional methods known to those of skill in the art. A subject having received a tissue transplant is especially susceptible to fungal infections from *Candida* species such as *Candida albicans*.

A subject having a central venous catheter is a subject having received a central venous catheter implant during a surgical procedure. A central venous catheter implant encompasses the use of conventional methods known to those of skill in the art. A subject having received a central venous catheter is especially susceptible to fungal infections from *Candida* species such as *Candida albicans*.

As used herein, the terms "compound" and "agent" are interchangeable.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof.

"Therapeutically effective amount" includes an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter)

or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent that is known to be useful for, or has been or is currently being used to prevent or impede the onset, development, and progression of disorder or symptoms.

In some instances the compounds described herein are useful also for treating a fungal infection in a subject. As used herein treating or treat is intended to include preventing, ameliorating, curing, reducing fungal growth or reducing symptoms, or preventing any increase in fungal growth or symptoms.

As used herein "reducing fungal growth" is intended to encompass an interference in fungal cell growth or processing which can be determined by a reduction in cell number, a reduction in cell division or a reduction in the yeast-to-hyphal transition phase.

5. DETAILED DESCRIPTION

Fungal infections are a huge clinical burden and highly prevalent among compromised host populations worldwide. *Candida albicans* is the major fungal pathogen in humans which cause both superficial mucosal and systemic mycoses with higher morbidity and mortality rates. For instance, mortality rate of systemic candidiasis among hospitalized patients could be as high as 70% under compromised conditions. Formation of long filamentous appendages known as hypha is a major virulent attribute that facilitates the tissue invasion of the fungus. Compounds that interfere with the formation of hypha serve as a novel approach to develop next generation of antifungal compounds. Expression profiling and genetic manipulation reveal that many of the genes that govern *C. albicans* biofilm development are required for the production of hyphae. On the other hand, hyphae are required for stable biofilm formation, which is even resistant to sonication. *C. albicans* mutants that have defects in the yeast-hyphal transition have a reduced ability to become internalized and to cause endothelial cell injury in vitro. Therefore, the hyphae formation is crucial for the biofilm stability and drug-resistance. Yeast-hyphal transition is a therapeutic target to solve the long existed drug resistance during anti-fungal treatment.

A large collection of small molecule library was screened in search of inhibitors of yeast-to-hypha transition (Y—H) of *C. albicans* using 384-well plate-high throughout assays (HTS). This screening assay, showed 20 molecules with Y—H inhibitory (Y-Hi) properties. After subsequent studies with robust Y—H inducing conditions, we herein report a novel small molecule SM21 (FIG. 1) with strong Y-Hi activity and antifungal-activity.

5.1 Antifungal Compound

Disclosed herein is a novel antifungal compound, a composition comprising the compound, a pharmaceutical composition comprising the compound, and a method of using the compound. In one embodiment, the compound is used to treat fungal infections.

Provided Herein is a Compound Having the Following Structure

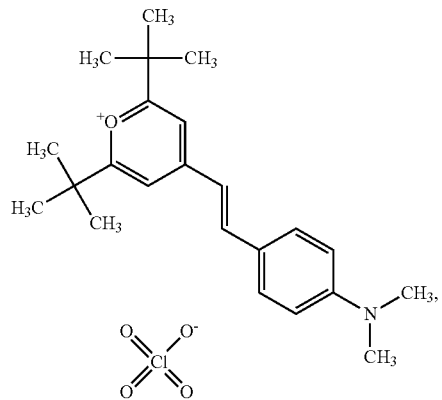 [SMILES: CN(C)c1ccc(/C=C/c2cc(C(C)(C)C)[o+]c(C(C)(C)C)c2)cc1 ; [O-][Cl+3]([O-])([O-])[O-]]

derivatives thereof; or a pharmaceutically acceptable salt, solvate, hydrate, stereoisomeric, tautomeric or polymorphic form thereof.

Those of skill in the art will recognize that compounds of structure:

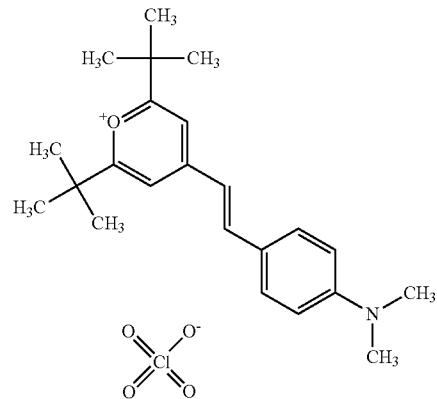 [SMILES: CN(C)c1ccc(/C=C/c2cc(C(C)(C)C)[o+]c(C(C)(C)C)c2)cc1 ; [O-][Cl+3]([O-])([O-])[O-]]

can be designed or prepared by reaction, e.g., via condensation or dehydration. For convenience, those of skill in the art will recognize that the compound e.g. of structure in FIG. 1F comprises a derivative, e.g. a radical of the anti-viral drug. Those derivatives can for example be prepared in a chemical reaction. Where appropriate, certain derivatives can be prepared by modification of the structure in FIG. 1F.

A pharmaceutically acceptable salt is readily prepared by mixing together solutions containing the free base and the desired acid. The salt generally precipitates from solution and is collected by filtration, or is recovered by evaporation of the solvent. The compounds of the structure (I) and their salts are anti-fungal agents, useful in the curative or prophylactic treatment of fungal infections in animals, including humans. For example, they are useful in treating topical fungal infections in man caused by, among other organisms, species of *Candida*, *Trichophyton*, *Microsporum* or *Epidermophyton*, or in mucosal infections caused by *Candida albicans* (e.g. thrush and vaginal candidiasis). They can also be used in the treatment of systemic fungal infections caused by, for example, species of *Candida* (e.g. *Candida albicans*), *Cryptocoous neoformans*, *Aspergillus flavus*, *Aspergillus fumigatus*, *Coccidioides*, *Paracoccidioides*, *Histoplasma* or *Blastomyces*.

In certain embodiments, the compound is a small molecule. In a specific embodiment, the compound is SM21 that inhibits yeast to hypha transition. In certain embodiments, the compound inhibits yeast to hypha transition under robust hyphal inducing conditions. In certain embodiments, the robust hyphal inducing conditions comprise lower concentration of the molecule, which is from 0.025 µg/ml to 0.2 µg/ml.

In one embodiment, provided herein are assays for phenotypic transition of *Candida* cells. In certain embodiments, the change is a morphological change. In certain embodiments, the change is from a budded form to a hyphal form. In other embodiments, the change is from a budded form to a pseudohyphal form. In still other embodiments, the change is from a pseudohyphal form to a hyphal form. In yet other embodiments, the change may be a morphological change from a hyphal form to a budded form, a pseudohyphal form to a budded form, or even a hyphal form to a pseudohyphal form.

In some embodiments, the change is an increase in the amount of cells in the first phenotypic form compared to the amount of cells in the second phenotypic form. In other embodiments, the measurable change is a decrease in the amount of cells in the second phenotypic form.

In certain embodiments, SM21 exhibits antifungal activity against wide range of fungal species at slightly higher concentrations. In certain embodiments, the concentration is 0.2-0.4 µg/ml, 0.4-0.6 µg/ml, 0.6-0.8 µg/ml, 0.8-1 µg/ml, 1-1.2 µg/ml, 1.2-1.4 µg/ml, 1.4-1.6 µg/ml, 1.6-1.8 µg/ml, 1.8-2 µg/ml, 2-4 µg/ml, 4-6 µg/ml, 6-6.25 µg/ml. In a specific embodiment, the concentration is 0.2-6.25 µg/ml. In one embodiment, the anti-fungal compound described herein is used as an anti-biofilm agent for fungal infections. In one embodiment, the anti-fungal compound is effective for treating local and systemic fungal infections of candidiasis. In one embodiment, SM21 is effective for treating local and systemic fungal infections of candidiasis. Safety of the compound described herein has been extensively evaluated using standard in vitro and in vivo assays which proved no-harmful effects. In certain embodiments, SM21 is a broad-spectrum anti-fungal agent for treating both local and systemic fungal infections. In certain embodiments, SM21 or pharmaceutically acceptable derivatives are used for the treatment of mycotic infections. In certain embodiments, SM21 or pharmaceutically acceptable derivatives thereof are used for the treatment of infections caused by various fungal pathogens including, but are not limited to *Candida*, *Cryptococcus*, *Aspergillus* and *Penicillium* species. In one embodiment, the fungal pathogen is *Candida albicans*.

The present invention discloses a novel antifungal agent that is used to treat fungal infections. Small molecule described herein (SM21) inhibits yeast-hyphal transition under robust hyphal inducing conditions at lower concentration of the molecule. In addition, SM21 exhibits antifungal activity against wide range of fungal species at slightly higher concentrations, including *C. albicans, C. glabrata, C. krusei, C. tropicalis, C. parapsilosis, C. neoformans, Aspergillus fumigates* and *Penicillium marneffei*. In certain embodiments, the concentration is 0.2-0.4 µg/ml, 0.4-0.6 µg/ml, 0.6-0.8 µg/ml, 0.8-1 µg/ml, 1-1.2 µg/ml, 1.2-1.4 µg/ml, 1.4-1.6 µg/ml, 1.6-1.8 µg/ml, 1.8-2 µg/ml, 2-4 µg/ml, 4-6 µg/ml, 6-6.25 µg/ml. In a specific embodiment, the concentration is 0.2-6.25 µg/ml. In a specific embodiment, SM21 showed superior antifungal activity on 16 multidrug resistant clinical isolates of *Candida* species. In a specific embodiment, the effect of the disclosed compounds, or more specifically, SM21, is highly specific to fungus and did not exert any anti-bacterial effect. In certain embodiments, the compound described herein is used in combination with other classes of anti-fungal compounds for the treatment of infections. These other classes of anti-fungal compounds are categorized according to their targets. Examples of these classes of anti-fungal compounds are indicated below:

| | Mechanism of action | Related antifungal agents | Commercial Drugs Examples |
|---|---|---|---|
| 1 | fungal cell wall components including ergosterol, Chitin, Glucan, mannoproteins fungal cell wall integrity | polyenes, azoles, chitin synthase inhibitors, glucan synthase inhibitors and manosyl transferase inhibitors. | Diflucan (Fluconazole, Pfizer), Vfend (Voriconazole, Pfizer), Amphotericin (Amphotericin B, Pharmacia), Cancidas (caspofungin acetate, Merk Sharp & Dohme) |
| 2 | Fungal protein synthesis: Elongation factors | Sordarins | NA |
| 3 | Adherins | Secreted aspertyl proteases inhibitors | NA |
| 4 | Immunoresponse | Antimicrobial peptides | Mycograb (efungumab Monoclonal antibody, Novartis, Phase III) |

Central Venous Catheters (CVC) and Urological Catheters (UCs) constituted the market for Antimicrobial Catheter Market. In US, about 200,000 cases of Blood Stream Infections (BSI) are directly related to CVCs; while 600,000 cases of Catheters Associated Urinary Tract Infection (CAUTI) are caused by UCs. The cause of catheters associated infection is the biofilm formation on the device surface. Such biofilm is usually the habitat for *Candida* spp. Therefore, antimicrobial (esp. anti-*Candida*) treatment of the device is a novel way to prevent catheter related infections. In certain embodiments, the compound described herein is used to coat and/or impregnated the devices. In certain embodiments, the compound is released in a sustained and/or controlled manner to combat the microbes presenting at the site.

In certain embodiments, the compound disclosed herein exhibits anti-biofilm activity against *Candida* mono or mixed species biofilms. In certain embodiments, the compound inhibits bacterial biofilm. In certain embodiments, the compound inhibits fungal biofilm. In certain embodiments, the compound inhibits bacterial biofilm to a greater extent than inhibits fungal biofilm. In specific embodiments, the compound disclosed herein exhibits anti-biofilm activity at 25 µg/ml. In specific embodiments, the compound disclosed herein exhibits anti-biofilm activity at 25 µg/ml while either biofilms was resistant to amphotericin B (32 µg/ml) and caspofungin (50 µg/ml). The compound disclosed herein has superior antifungal activity than existing antifungal agents such as amphotericin B and caspofungin for *Candida* biofilms. In certain embodiments, the compound disclosed herein also successfully protected human keratinocytes *Candida* infection in *Candida*-human oral keratinocytes co-culture model.

In certain embodiments, the compounds as provided herein are used for treatment of biofilm-associated infections. In certain embodiments, the biofilm infection is bacterial. In certain embodiments, the biofilm infection is fungal. In certain embodiments, the biofilm infection is both bacterial and fungal. In certain embodiment, the biofilm is formed on natural and abiotic surfaces. In certain embodiments, the biofilm is formed on a medical device. In certain embodiments, the biofilm is formed on an implant. In certain embodiments, the biofilm is formed on dental implants or dentures. In certain embodiments, the biofilm is formed on bioprosthetic materials, such as polymethylmethacrylate and silicone elastomer.

In certain embodiments, SM21 exhibits anti-biofilm activity against *Candida* mono or mixed species biofilms. In specific embodiments, SM21 exhibits anti-biofilm activity at 25 µg/ml. In specific embodiments, SM21 exhibits anti-biofilm activity at 25 µg/ml while either biofilms was resistant to amphotericin B (32 µg/ml) and caspofungin (50 µg/ml). SM21 has superior antifungal activity than existing antifungal agents such as amphotericin B and caspofungin for *Candida* biofilms. In certain embodiments, SM21 also successfully protected human keratinocytes *Candida* infection in *Candida*-human oral keratinocytes co-culture model.

In a specific embodiment, SM21 showed no cytotoxicity in human oral keratinocytes, gingival fibroblasts and monocytes at effective concentration. In a specific embodiment, mice treated with 100 times of the effective dose did not show any detrimental effect in terms of weight reduction and side effects.

In a specific embodiment, SM21 replaces existing anti-fungal agents and overcome the current drug resistant dilemma in antifungal therapy. In a specific embodiment, SM21 is used in combination with other anti-fungal compounds.

5.2 Combination Therapy

The compounds as described herein may optionally be delivered with other antifungal agents in the form of anti-fungal cocktails, or individually, yet close enough in time to have a synergistic effect on the treatment of the infection. An antifungal cocktail is a mixture of any one of the compounds described herein with another antifungal drug. In one embodiment, a common administration vehicle (e.g., tablet, implants, injectable solution, injectable liposome solution, etc.) is used in for the compound as described herein and other antifungal agent(s).

Anti-fungal agents are useful for the treatment and prevention of infective fungi. Anti-fungal agents can be classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Other antifungal agents include Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Cancidas (Caspofungin Acetate), Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

In certain embodiments, the compound described herein can be used alone or in combination with one or more antifungal compounds as shown below:

| Pat. No. | Patent Name | Chemical Structure |
|---|---|---|
| US20060194769A1 | Small molecules that reduce fungal growth | 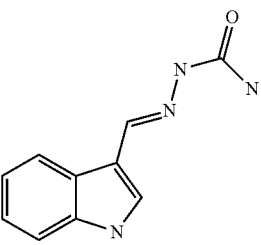 [SMILES: NC(=O)N/N=C/c1c[nH]c2ccccc12] |

-continued
| Pat. No. | Patent Name | Chemical Structure |
|---|---|---|
| US20040106663A1 | Inhibitors of fungal invasion | 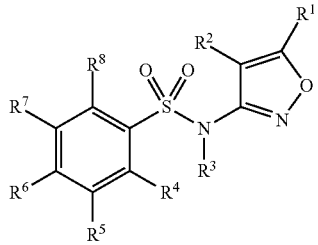<br>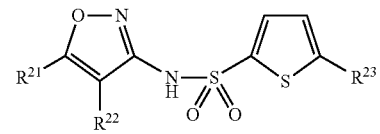 |
| U.S. Pat. No. 7,825,143 B2 | Methods for controlling the yeast-to-filamentous growth transition in fungi | 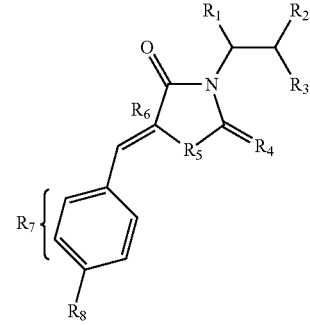 |
| US20060154991A1 | Inhibiting of *Candida albicans* | 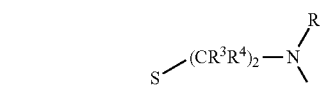<br>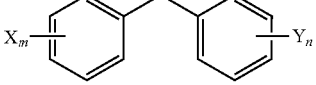<br>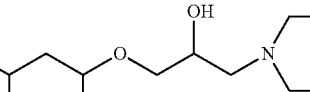<br>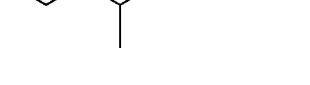 |

| Pat. No. | Patent Name | Chemical Structure |
|---|---|---|
| | | 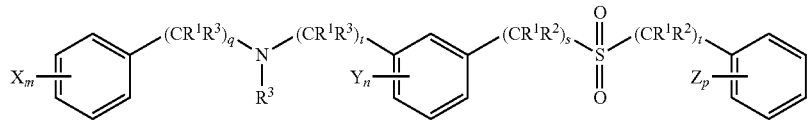 |
In certain embodiments, the compounds described herein are used in combination with one or more antifungal compounds as shown below:
| Molecule (IC$_{100}$) | Chemical Structure |
|---|---|
| A-3 (60 µM) | 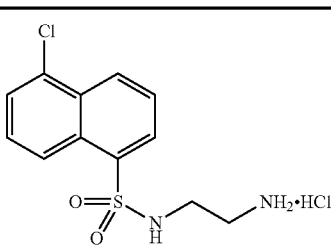 |
| W7 (40 µM) | 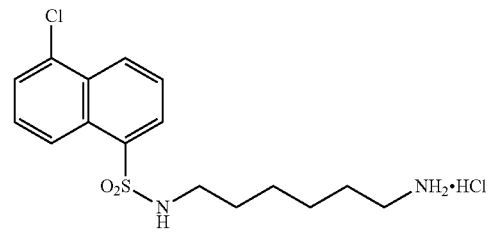 |
| Tyrphostin AG1478 (80 µM) | 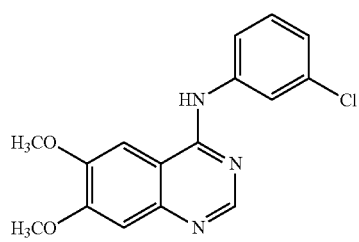 [SMILES: COc1cc2ncnc(Nc3cccc(Cl)c3)c2cc1OC] |
| Tyrphostin 9 (80 µM) | 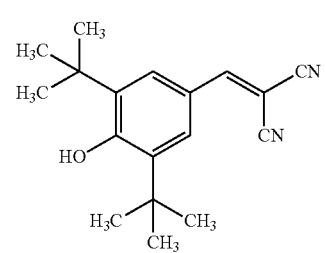 [SMILES: CC(C)(C)c1cc(C=C(C#N)C#N)cc(C(C)(C)C)c1O] |
| GW 5074 (60 µM) | 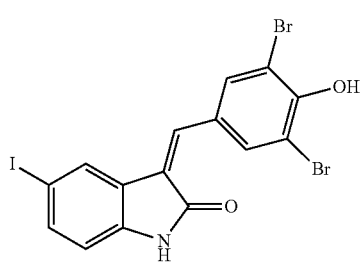 [SMILES: O=C1Nc2ccc(I)cc2/C1=C/c1cc(Br)c(O)c(Br)c1] |

-continued
| Molecule (IC$_{100}$) | Chemical Structure |
|---|---|
| FK506 (60 µM) | 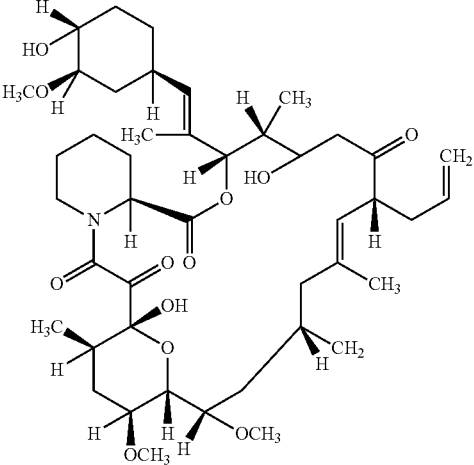 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)C(O)CC1=O)[C@H](C)C[C@@H]2OC] |
| L-744,832 (130 µM) | 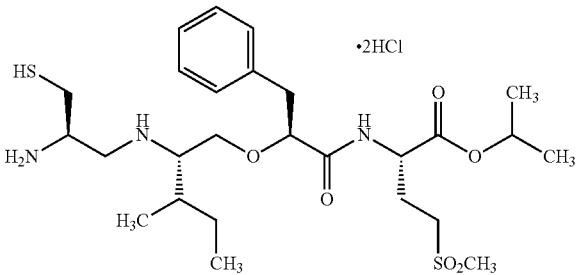 [SMILES: CCC(C)[C@@H](CO[C@@H](Cc1ccccc1)C(=O)N[C@@H](CCS(C)(=O)=O)C(=O)OC(C)C)NC[C@@H](N)CS] |
| Clozapine (50 µM) | 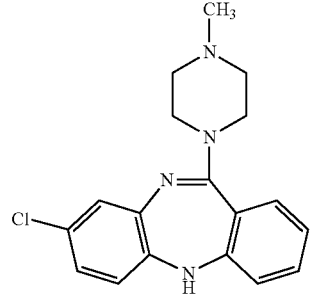 [SMILES: CN1CCN(C2=Nc3cc(Cl)ccc3Nc3ccccc32)CC1] |
| Fluspirilene (40 µM) | 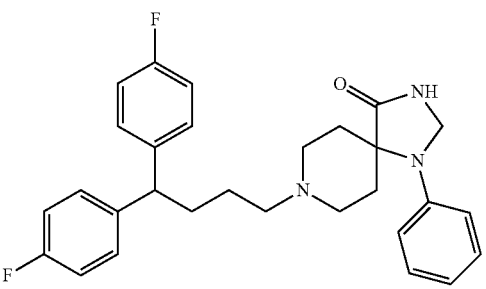 [SMILES: O=C1NCN(c2ccccc2)C12CCN(CCCC(c1ccc(F)cc1)c1ccc(F)cc1)CC2] |
| GW 9662 (130 µM) | 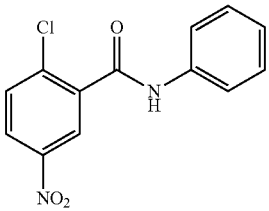 [SMILES: O=C(Nc1ccccc1)c1cc([N+](=O)[O-])ccc1Cl] |

-continued

| Molecule (IC$_{100}$) | Chemical Structure |
|---|---|
| ETYA (12 μM) | 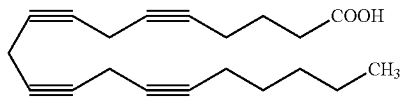 [SMILES: CCCCCC#CCC#CCC#CCC#CCCCC(=O)O] |
| CGP-37157 (40 μM) | 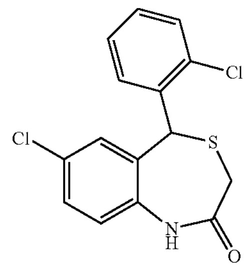 [SMILES: O=C1CSC(c2ccccc2Cl)c2cc(Cl)ccc2N1] |
| TMB-8 (40 μM) | 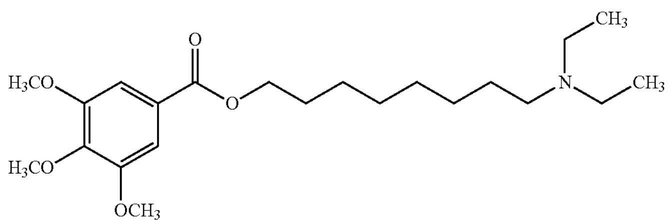 [SMILES: CCN(CC)CCCCCCCCOC(=O)c1cc(OC)c(OC)c(OC)c1] |
| Nigericin (130 μM) | 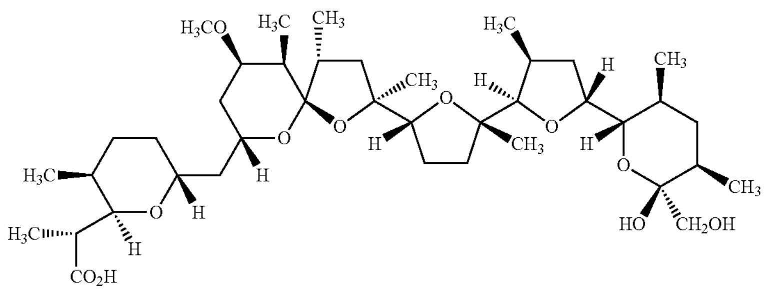 [SMILES: CO[C@@H]1C[C@@H](C[C@H]2CC[C@H](C)[C@H]([C@@H](C)C(=O)O)O2)O[C@]2(O[C@](C)([C@H]3CC[C@@](C)([C@@H]4O[C@@H]([C@H]5O[C@@](O)(CO)[C@H](C)C[C@@H]5C)C[C@@H]4C)O3)C[C@H]2C)[C@@H]1C] |
| YC-1 (60 μM) | 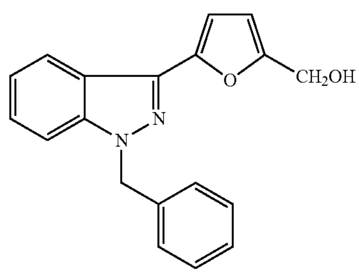 [SMILES: OCc1ccc(-c2nn(Cc3ccccc3)c3ccccc23)o1] |
| HA14-1 (20 μM) | 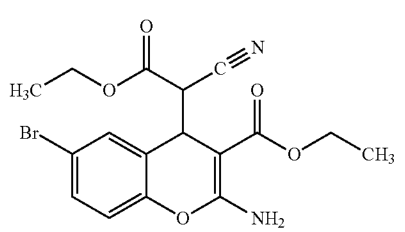 [SMILES: CCOC(=O)C1=C(N)Oc2ccc(Br)cc2C1C(C#N)C(=O)OCC] |

In certain embodiments, the compound described herein is used in combination with one or more antifungal compounds. Antifungal compounds include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; PyrroInitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

In certain embodiments, the use of a combination of more than one antifungal compounds has a synergistic effect. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

5.3 Pharmaceutical Compositions and Methods of Administration

The compound disclosed herein can be formulated into pharmaceutical compositions using methods available in the art and those disclosed herein. Such compounds can be used in some embodiments to enhance delivery of the drug to the subject.

The methods provided herein encompass administering pharmaceutical compositions containing at least one compound as described herein, including a compound of structure I, if appropriate in the salt form, either used alone or in the form of a combination with one or more compatible and pharmaceutically acceptable carriers, such as diluents or adjuvants, or with another antifungal agent. In certain embodiments, the second agent can be formulated or packaged with the compound provided herein, according to those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art. In clinical practice the active agents provided herein may be administered by any conventional route, in particular orally, parenterally, rectally or by inhalation (e.g. in the form of aerosols). In certain embodiments, the compound provided herein is administered orally. Use may be made, as solid compositions for oral administration, of tablets, pills, hard gelatin capsules, powders or granules. In these compositions, the active product is mixed with one or more inert diluents or adjuvants, such as sucrose, lactose or starch. These compositions can comprise substances other than diluents, for example a lubricant, such as magnesium stearate, or a coating intended for controlled release. Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products. The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium. The compositions for rectal administration are suppositories or rectal capsules which contain, in addition to the active principle, excipients such as cocoa butter, semi-synthetic glycerides or polyethylene glycols. The compositions can also be aerosols. For use in the form of liquid aerosols, the compositions can be stable sterile solutions or solid compositions dissolved at the time of use in sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose. In one embodiment, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and one or more pharmaceutically acceptable carriers or excipients. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents. Lactose free compositions provided herein can comprise excipients that are well known in the art and are listed, for example, in the U.S. Pharmocopia. In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate. Further encompassed herein are anhydrous pharmaceutical compositions and dosage forms comprising active ingredients, since water can facilitate the degradation of some compounds. Anhydrous pharmaceutical compositions and dosage forms provided herein can be prepared using anhydrous or low moisture containing ingredients and low moisture or low humidity conditions. An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs. The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject. A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject. The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000). Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound. Oral Dosage Forms Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, provided herein is a hand sanitizing composition comprising the compounds disclosed herein. In certain embodiments, provided herein is a lotion comprising the compounds as disclosed herein.

5.3.1 Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompasseed herein are single unit dosage forms suitable for oral administration such as, but not limited to, tablets, capsules, gelcaps, and caplets that are adapted for controlled release. All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects. Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds. In certain embodiments, the drug may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

5.3.2 Parenteral Dosage Forms

In one embodiment, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate. Compounds that increase the solubility of one or more of the active ingredients disclosed herein can also be incorporated into the parenteral dosage forms.

5.3.3 Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16.sup.th, 18.sup.th and 20.sup.th eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients. Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16.sup.th, 18.sup.th and 20.sup.th eds., Mack Publishing, Easton Pa. (1980, 1990 & 2000). Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate). The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

5.4 Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing a fungal infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In one embodiment, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses. In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL. In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months. In certain aspects, provided herein are unit dosages comprising a compound, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art. The dosages of the second agents are to be used in the combination therapies provided herein. In certain embodiments, dosages lower than those which have been or are currently being used to prevent or treat fungal infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9.sup.th Ed, Mc-Graw-Hill, New York; Physician's Desk Reference (PDR) 57.sup.th Ed., 2003, Medical Economics Co., Inc., Montvale, N.J., which are incorporated herein by reference in its entirety. In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In various embodiments, the therapies are administered no more than 24 hours apart or no more than 48 hours apart. In certain embodiments, two or more therapies are administered within the same patient visit. In other embodiments, the compound provided herein and the second agent are administered concurrently. In other embodiments, the compound provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the compound provided herein and the second active agent exert their effect at times which overlap. Each second active agent can be administered separately, in any appropriate form and by any suitable route. In other embodiments, the compound provided herein is administered before, concurrently or after administration of the second active agent. In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment. In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day. The second agent can act additively or synergistically with the compound provided herein. In one embodiment, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

5.5 Kits

Also provided are kits for use in methods of treatment of a fungal infection. The kits can include a compound or composition provided herein, a second agent or composition, and instructions providing information to a health care provider regarding usage for treating the infection. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition. In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

The kits described herein contain one or more containers, which contain compounds, signaling entities, biomolecules and/or particles as described. The kits also contain instructions for mixing, diluting, and/or administrating the compounds. The kits also include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits comprise a carrier being compartmentalized to receive in close confinement one or more container such as vials, tubes, and the like, each of the container comprising one of the separate elements to be used in the method. For example, one of the container may comprise a positive control in an assay. Additionally, the kit may include containers for other components, for example, buffers useful in the assay.

The following Examples illustrate the synthesis and use of representative compounds provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

5.6 Methods of Making SM21 and its Derivatives

All of the above reactions are conventional and appropriate reagents and reaction conditions for their performance and procedures for isolating the desired products will be well known to those skilled in the art, in accordance with literature.

5.7 Assays for Testing Antifungal Compounds

The in vitro evaluation of the antifungal activity of the compounds can be performed by determining the minimum inhibitory concentration (m.i.c.), which is the concentration of the test compound, in a suitable medium, at which growth of the particular micro-organism fails to occur. In practice, a series of agar plates, each having the test compound incorporated at a particular concentration, is inoculated with a standard culture of, for example, *Candida albicans*, and each plate is then incubated for 48 hours at 37° C. The plates are then examined for the presence or absence of growth of the fungus and the appropriate m.i.c. value is noted. Other micro-organisms used in such tests can include *Aspergillus fumigatus, Trichophyton* sp., *Microsporum* spp., *Epidermophyton floccosum, Coocidioides immitis* and *Torulopsis glabrata*.

The in vivo evaluation of the compound can be carried out at a series of dose levels by intraperitoneal or intravenous injection, or by oral administration, to mice which are inoculated with, e.g., a strain of *Candida albicans* or *Aspergillus fumigatus*. Activity is based on the survival of a treated group of mice after the death of an untreated group of mice. The dose level at which the compound provides 50% protection against the lethal effect of the infection is noted.

5.8 Method of Treatment and Prevention

Provided herein is a method of reducing growth of a fungus or bacteria by administering one or more compounds provided herein. The method comprises contacting a cell with one or more compounds as described herein in an amount effective to reduce the growth of a fungus. Provided herein are methods for treating a fungal infection in a subject by administering to a subject in need thereof the compounds described herein in an amount effective to reduce the growth of a fungus. In certain embodiments, the compounds described herein are used to treat Candia related diseases, including but are not limited to, irritable bowel syndrome, chronic sinusitis, chronic fatigue syndrome, fibromyalgia, thrush, eczema, atopic dermatitis, autism, leaky gut syndrome, Crohn's disease, ulcerative colitis, interstitial cystitis, genitourinary diseases, and celiac disease. Skin infections caused by *Candida* may be found in the diaper area in babies, in the armpits, groin, and underneath the breasts, at the corners of the mouth (angular cheilitis), in toenails, or at the edge of the nails (paronychia). In certain embodiments, the method of treatment and prevention using the compounds for subjects with a weakened immune system due to certain medicines and diseases, such as AIDS, HIV, diabetes and obesity.

5.9 Methods of Coating a Medical Device

The compounds that are provided herein can be used to treat a variety of medical devices, such as catheters, as well as industrial surfaces. Fungus can form biofilm on intravascular catheters and other medical implants These biofilms enhance antimicrobial resistance and can render infections refractory to antifungal therapy. Persistence of an infection can necessitate removal of the device, which can be undesirable or even life threatening. Therefore, provided herein is a method of coating a medical device using the compounds described herein on the materials or surfaces of the medical device that mitigate or prevent fungal colonization or infection with subsequent biofilm formation. The method comprises applying the composition described herein on the surface of a medical device. In certain embodiments, the composition adheres to the surface of a medical device. In certain embodiments, the composition is coated in the medical device.

In certain embodiments, provided herein is a composition comprising a paint and one or more compounds as described herein. Also provided is a method of modifying a surface of a medical device. The method comprises providing one or more coatings of a composition, comprising one or more compounds as described herein, to at least a portion of the surface of a medical device to form a coated surface region. In certain embodiments, the composition comprises a paint and one or more compounds. In certain embodiments, the method comprises adding one or more compounds as described herein to a paint; obtaining a composition comprising paint and one or more compounds as additives; coating a medical device or an industrial surface with the paint comprising the compounds. In certain embodiments, the medical device is an implantable medical device. In certain embodiments, the industrial surface is stainless steel. In certain embodiments, the industrial surface is plastic. In certain embodiments, the industrial surface is a surgical table. In certain embodiments, the medical device is a surgical instrument.

6. EXAMPLES

The following Examples showed the potent antifungal properties of an embodiment described herein, -SM21, against fungal infections.

6.1 Study 1: Yeast-to-Hypha Inhibitory Properties of SM21 Under Strong Hyphal Inducing Conditions Several environmental conditions which are known to induce the hyphal formation of *C. albicans* such as serum, Lee's medium, Spider medium, temperature and 37° C. were used to test the ability of SM21 to inhibit Y—H transition.

(A) Control samples showing *C. albicans* hyphal formation (B) Test samples were incubated with SM21 at Y-Hi concentration showing yeast morphology (C-E) *C. albicans* clinical strains A15 (C), H2 (D) and H11 (E) incubated with SM21 at Y-Hi concentration for 24 h. SM21 could act as a Y-Hi at a lower concentration of 0.025 μg/ml and 0.0.5 μg/ml for $10^4$ cells/ml and $10^6$ cells/ml of *C. albicans*, respectively. Chemical structure of SM21 is shown in (F)

6.2 Study 2: Anti-Fungal Activity of SM21

Antifungal activity of the small molecules was evaluated using USA standards, Clinical and Laboratory Standards Institute (CLSI) criteria. In brief, inocula from 24 h *Candida* cultures on Sabourauds's dextore agar were standardized to a turbidity equivalent of 0.5 McFarland standards at 520 nm with a spectrophotometer. The suspensions were further diluted in Rosewell Park Memorial Institute (RPMI) 1640 medium (Life technologies, New York, USA) to yield an inoculum concentration of approximately 0.5 $1 \times 10^3$ to 2.5 $1 \times 10^3$ cells/ml. Minimum inhibitory concentration (MIC) and minimum fungicidal concentration (MFC) assay was performed in 96-well plates (Iwaki, Tokyo, Japan) and each of the *Candida* species was exposed to a double dilution of SM21. Amphotericin B was used as a positive control. All the experiments were preformed three occasions with duplicates for all isolates. The plates were incubated at 35° C. for 48 h to evaluate MIC. In the case of Cryotococcus neoformans, reading were taken after 72 h. Aforementioned assay was performed for *C. albicans* ATCC 90028, *C. albicans* SC5314 and 10 *C. albicans* clinical isolates. Moreover, MIC/MFC determination was carried out for other fungal species such as *C. glabrata*, *C. krusei*, *C. tropicalis*, *C. parapsilosis*, *C. neoformans*, *Aspergillus fumigates* and *Penicillium marneffei*. SM21 had a potent antifungal activity of all the fungal species tested showing its broad spectrum activity (Table 1). We further tested antifungal activity of SM21 against 20 *C. albicans* strains isolated from HIV/AIDS patients and SM21 was active against all isolates. Next using dose-dependent assay we tested that MIC/MFC of SM21 from $10^3$ cells/ml to $10^7$ cells/ml of *C. albicans* (Table 2). Each of the foregoing experiment was repeated on three different occasions.

TABLE 1

Susceptibility of fungal species (MIC90) to SM21 at a concentration of 0.5 cFarland inoculums ($10^6$ cells/ml)

| Fungal species | SM21 (μg/ml) | Amphotericin B (μg/ml) |
|---|---|---|
| *C. albicans* ATCC 90028 | 0.2 | 0.2 |
| *C. albicans* SC5314 | 0.2 | 0.2 |
| *C. albicans* CL1 | 0.2 | 0.2 |
| *C. albicans* CL2 | 0.2 | 0.4 |
| *C. albicans* CL3 | 1.6 | 0.4 |
| *C. albicans* CL3 | 1.6 | 0.4 |
| *C. albicans* CL4 | 0.8 | 0.2 |
| *C. albicans* CL5 | 1.6 | 0.2 |
| *C. albicans* CL6 | 1.6 | 0.2 |
| *C. albicans* CL7 | 0.8 | 0.2 |
| *C. albicans* CL8 | 0.8 | 0.4 |
| *C. albicans* CL9 | 1.6 | 0.4 |
| *C. albicans* CL10 | 1.6 | 0.2 |
| *C. glabrata* ATCC | 1.6 | 0.4 |
| *C. krusei* ATCC | 0.4 | 0.4 |
| *C. tropicalis* ATCC | 0.8 | 0.8 |
| *C. parapsilosis* ATCC | 1.6 | 0.8 |
| *C. neoformans* | 0.4 | 0.4 |
| *Aspergillus fumigatus* | 6.25 | 1.56 |
| *Penicillium marneffei* | 0.2 | 0.05 |

TABLE 2

Dose-dependent assay for yeast-to-hyha inhibitory activity (Y-Hi) and antifungal activity of SM21

| Cell density | SM21 Y-Hi | SM21 MIC/MFC | Amphotericin B MIC/MFC |
|---|---|---|---|
| C. albicans $10^4$ cells/ml | 0.025 | 0.1 | 0.2 |
| C. albcians $10^5$ cells/ml | 0.5 | 0.1 | 0.2 |
| C. albicans $10^6$ cells/ml | 0.1 | 0.2 | 0.2 |
| C. albicans $10^7$ cells/ml | 0.2 | 0.6 | 0.8 |

Figure 3:
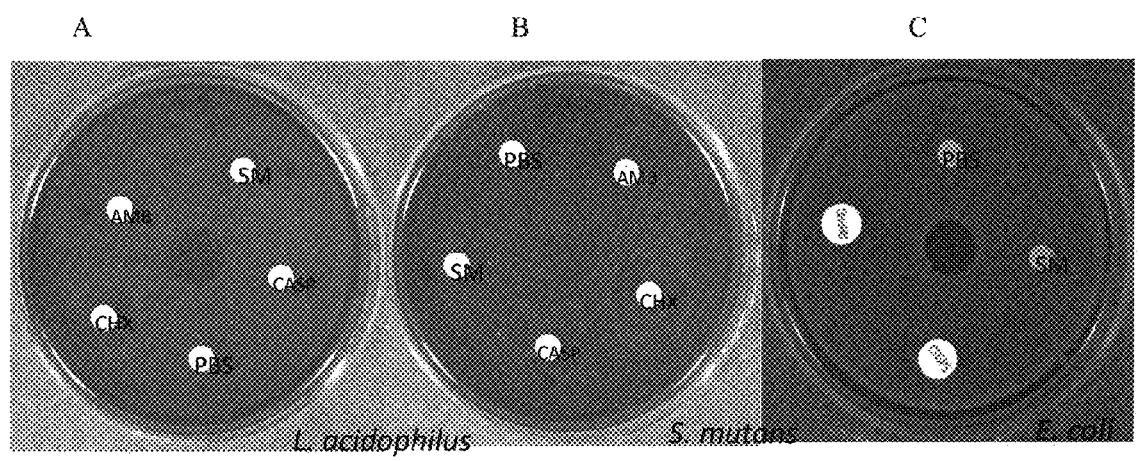

Oral Biosciences laboratory has one of the largest collections of fungal isolates, particular that of *Candida* species in the world. In our previous studies, we have found multidrug resistant clinical isolates of *Candida* species against existing antifungals. In particular, some of these strains are resistant to best antifungal agents to date such as caspofungin, amphotericin B and fluconazole. Therefore, we performed antifungal susceptibility testing for SM21 against these drug resistant *Candida* isolates suing CLSI M27A brothmicrodultion assay and CLSI M44-A disc diffusion assay. These studies clearly demonstrated that SM21 has superior antifungal activity than existing antifungal agents (Table 2, FIG. 2) However, at the effective concentration of the fungi, it does not exert any antibacterial effect showing fungal specific activity of the compound (FIG. 3).

TABLE 3

Efficacy of SM21 against multidrug resistant clinical isolates of *Candida* species

| Drug resistant isolates | Resistant antifungals | MIC of SM21 (µg/ml) |
|---|---|---|
| C. albicans T1675 | Fluconazole, Itraconazole | 0.5 |
| C. parapsilosis T1677 | Caspofungin, fluconazole, Itraconazole, Ketaconazole, Voriconazole | 1 |
| C. parapsilosis T1565 | Caspofungin, Itraconazole | 1 |
| C. parapsilosis T1545 | Caspofungin | 1 |
| C. parapsilosis T1688 | Itraconazole | 0.5 |
| C. glabrata T1585 | Fluconazole, Itraconazole, ketoconazole, Voriconazole | 1 |
| C. glabrata T1672 | Itraconazole, Ketaconazole | 0.5 |
| C. glabrata 1570 | Itraconazole | 0.5 |
| C. tropicalis T1427 | Itraconazole | 1 |
| C. tropicalis T789 | Itraconazole | 1 |
| C. tropicalis T1148 | Itraconazole | 0.5 |
| C. krusei 1472 | Fluconazole, Itraconazole, ketaconazole | 1 |
| C. krusei 1266 | Fluconazole | 0.5 |
| C. krusei T1562 | Fluconazole | 1 |
| C. krusei 1266 | Fluconazole | 1 |
| C. guilliermondii T1549 | Caspofungin, Amphotericin B, Fluconazole | 1 |

6.3. Study 3: SM21 Exhibits Anti-Biofilm Activity Against *Candida* Biofilms 6.3.1 Mono Species Biofilms:

Although most of the existing antifungals work effectively against planktonic mode of *Candida*, those are less effective against the biofilm mode of growth. For instance, we have previously shown the resistance of *Candida* biofilms against amphotericin and caspofungin. Therefore, next using standard biofilm assays we have established in our laboratory, we examined the effect of SM21 against *Candida* biofilms. In brief, *Candida* cells were grown in SDA medium at 37° C. for 18 h. Then a loopful of the yeast was inoculated into the yeast nitrogen base (YNB; Difco) medium supplemented with 50 mM glucose in a rotary shaker at 75 rpm. After overnight broth culture, the yeasts were harvested in the late exponential growth phase and washed twice with 20 ml of phosphate buffer saline (PBS; pH 7.2. 0.1 M) prior to use in the biofilm studies. *Candida* biofilms were developed according to a previously published protocol. In brief, washed yeast cells were resuspended in YNB supplemented with 100 mM glucose and adjusted to an optical density of 0.38 at 520 nm ($1 \times 10^7$ cells/ml). The standard cell suspension was used immediately to develop biofilms on commercially available presterilized, polystyrene, 96-well plate (IWAKI, Tokyo, Japan). At first, 100 µl of standardized cell suspension ($1 \times 10^7$ cells/ml) was pipetted into each well of a microtiter plate and incubated for 1.5 h at 37° C. in a shaker at 75 rpm to permit yeast adherence to the well surface (adherence phase). For controls, a well of each microtiter plate was handled in an identical fashion except that no *Candida* suspension was added. Following the adhesion phase, the cell suspensions were aspirated, and each well washed with 100 µl of PBS to remove loosely adherent cells. 200 µl of YNB with 100 mM glucose were then pipetted into each of the washed wells and the plates incubated at 37° C. in a shaker at 75 rpm for 24 or 48 h. After biofilm growth phase microscopic examination of the cultures were performed to rule out contamination. Then, the suspending medium was aspirated and biofilms were washed with 100 µl PBS to remove the nonadherent cells. The stock solutions were diluted twofold with RPMI 1640 supplemented with 2% glucose to obtain SM21 concentration from 100 to 0.2 µg/ml drug concentrations. In parallel, other antifungal agents such as caspofungin (100 to 0.1 µg/ml) and amphotericin B (240 µg/ml to 0.225 µg/ml) was also prepared as describe above. A total of 100 µl of drug solution was added to the microtiter plate containing *Candida* biofilms. Biofilms were then incubated at 37° C. for 24 h with the antifungals and afterwards metabolic activity of fungal cells was determined by the XTT [2,3-bis(2-methoxy-4-nitro-5-sulfophenyl)-2H-tetrazolium-5-carboxanilide sodium salt] assay (17, 28). *Candida* biofilm MIC90 was defined as the lowest drug concentration with 90% reduction in opacity compared with the drug free control. Each experiment was repeated three times with four replicates.

SM21 showed potent anti-biofilm activity against 24 h *C. albicans* biofilms as MIC90 were is 3.2 µg/ml. In contrast, *C. albicans* biofilms were resistant to amphotericin B (32 µg/ml) and caspofungin (50 µg/ml). This experiment clearly showed that SM21 was has superior antifungal activity than existing antifungals amphotericin B and caspofungin for *Candida* biofilms. At 48 h, *Candida* biofilms were more resistant to antifungal agents. However, SM21 had the best effective concentration compared to existing antifungal agents.

TABLE 4

Minimum inhibitory concentration of 48 h *Candida* biofilms against existing antifungal agents and SM21 (µg/ml)

| Candida species | Caspofungin | Amphotericin B | Ketoconazole | 5-fluorocytosine | SM21 |
|---|---|---|---|---|---|
| C. albicans | 100 | 32 | 64 | 420 | 25 |
| C. glabrata | 100 | 16 | 64 | 420 | 25 |
| C. krusei | 100 | 32 | 64 | 250 | 25 |

6.3.2 Mixed Species Biofilms

Clinical studies have shown that some of the *Candida* species could involve mixed *Candida* species such as *C.*

*albicans* with non-albicans *Candida* species. Therefore, next we formed mixed species biofilms using the methods we have used in our previous published studies. This methodology is essentially similar to what mentioned under monospecies biofilms except initial inoculums involve two *Candida* species at equal inoculums size of 1×10⁷ cells/ml. After 48 h of growth, mixed species *Candida* biofilms were subjected to serially diluted concentration of SM21 and MIC was determined by XTT reduction assay (FIG. 5). This study showed SM21 is equally active against mixed species *Candida* biofilms at the concentration of 25 µg/ml showing its promising role as anti-biofilm agent against fungal biofilms.

6.4. Study 4: Cytotoxicty Assay and In Vivo Experiments Confirming the Safety of SM21

Standard Vero cell line was used as well as other primary culture cells such as human oral keratinocytes, human gingival fibroblasts and human monocytes which showed that no cytotoxicity of SM21 at effective concentration (FIG. 6). Next, we used mouse model and treated the animals with 100 times of the effective dose (2 µg) i.e. 200 µg of SM21 twice a day for five days. This experiment did not show any detrimental effect of SM21 in terms of weight reduction and side effects confirming its safety under in vivo conditions.

6.5 Study 5: SM21 Prevent *Candida* Infection in *Candida*-Human Oral Keratinocytes Co-Culture Model We also examined the ability of SM21 to inhibit invasion of *Candida albicans* in *Candida*-human oral keratinocytes co-culture model. Primary human oral keratinocytes (ScienCell Research Laboratories™, Carlsbad, Calif., USA) at passage two were cultured using Defined Keratinocyte-Serum Free Medium (Gibco, Grand Island, N.Y., USA) which contained 0.2% Defined Keratinocyte-SFM Growth Supplement (Gibco) and 1% penicillin/streptomycin solution. Cells were incubated at 37° C. in a humidified atmosphere with 5% $CO_2$ and 95% air. Yeast cells for inoculation were cultured for 24 h at 37° C. on Sabouraud dextrose agar (Difco, Hampshire, England). A sample of the culture was washed thrice in PBS and an inoculum of approximately 2×10⁵ cells was suspended in 10 ml of YPG medium (1% yeast extract, 2% peptone and 2% glucose; Difco, Detroit, Mich.). The suspension was cultured for 18 h at 37° C. with orbital shaking and the cells were harvested, washed in 0.9% NaCl and a sample of cells was resuspended in fresh medium in a shaker for 24 h at 37° C. Afterwards the cells were harvested by centrifuge and the inocula were prepared in phosphate buffered saline (PBS, pH 7.2). Human oral keratinocytes were grown to 80-90% confluence in u-Slide 8-well plates (ibidi GmbH Integrated BioDiagnostics, Martinsried, Germany). 1×10⁴ cells/ml *C. albicans* cells were added to the wells and incubated with the cells at 37° C. in 5% $CO_2$ and 95% air. Test samples were treated with SM21 together with *C. albcians*. After 24-h incubation, cells were treated with Calcein AM (1 uM) and EthD-1 (2 uM) from the LIVE/DEAD® Viability/Cytotoxicity Kit (Invitrogen Corp., Carlsbad, Calif., USA). After 30 minutes of treatment, the proportion of dead keratinocytes in each well was examined by using a confocal laser scanning microscope. This study showed that SM21 is able to prevent the epithelial cell damage from *C. albicans* invasion (FIG. 7) (A) control samples showing *Candida* hyphae and dead keratinocytes (B) samples treated with SM21 showing live keratinocytes. This study demonstrated therapeutic potential of SM21 in local *Candida* infection such as mucous membrane candidiasis.

6.6. Study 6: In Vivo Anti-Fungal Activity Using Systemic Candidiasis Mouse Model As a pilot study, we used systemic candidiasis mouse models we have established in our laboratory to evaluate the effect of SM21 against systemic *Candida* infection. In brief, *C. albicans* inoculum of 1×10⁶ cells/mL was prepared in phosphate buffered saline (PBS) eight mice were infected with 100 µl of the standard inoculum size intravenously via the tail vein. Three hours after post-infection four mice (test group) were given 2 µg of SM21 and other four (control group) were given PBS. SM21 treatment was continued twice a day for five days. By five days all mice in the control group died (FIG. 8). Mice in each test group were sacrificed according to the standard guidelines and their kidney, liver, pancreas, and spleen will be harvested. The fungal burden in the tissues will be assessed according to a standard protocol. In brief, part of the excised tissues were weighed individually and homogenized in sterile saline. Aliquots of 100 µL from tissue homogenates and their dilutions were plated on Sabouraud's dextrose agar and colonies were counted after 48 h of incubation at 37° C.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A method for reducing growth of a fungus comprising contacting a fungal cell with a compound having a structure:

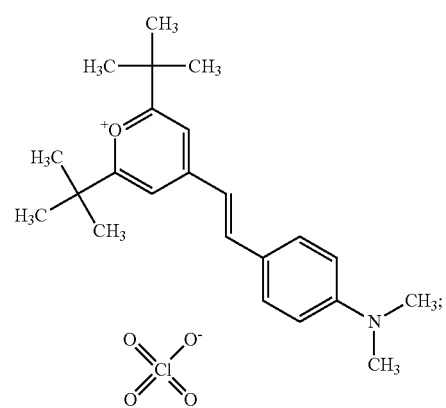 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier, wherein the fungal cell is *Candida albicans, Candida glabrata, Candida krusei, Candida tropicalis, Candida parapsilosis, Candida neoformans, Aspergillus fumigates*, or *Penicillium marneffei*.

2. The method of claim 1 wherein the fungal cell is a pathogen.

3. A method of treating and preventing against fungal infections in a subject which comprises administering to the subject an effective amount of a compound having the structure:

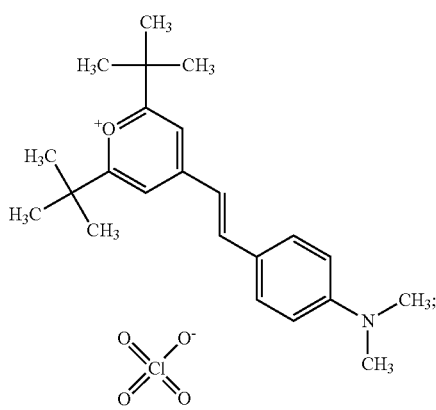 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier, wherein the fungal infection is caused by at least one of *C. albicans, C. glabrata, C. krusei, C. tropicalis, C. parapsilosis, C. neoformans, Aspergillus fumigates* and *Penicillium marneffei*.

4. The method of claim 3 wherein the fungal cell is a pathogen.

5. The method of claim 3, wherein the subject is a human.

6. The method of claim 5, wherein the subject is immunocompromised.

7. The method of claim 5, wherein the subject had received chemotherapy.

8. The method of claim 5, wherein the subject has AIDS.

9. The method of claim 5, wherein the subject had received a transplant.

10. The method of claim 5, wherein the subject has a central venous catheter.

11. The method of claim 5, wherein the compound is administered via injection, topical route, oral route, nasal route, aerosol, or enema route.

12. A method for reducing growth of a fungus comprising contacting a fungal cell with a compound having a structure:

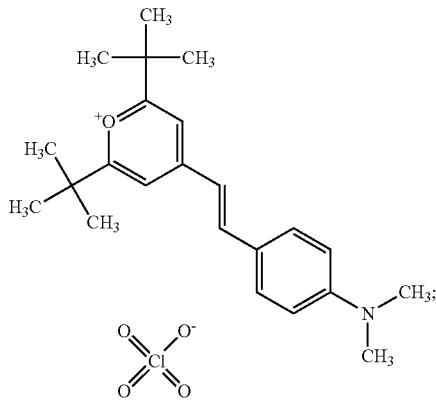 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier, wherein the fungal cell is a species of the genus *Candida*.

13. The method of claim 12, wherein the fungal cell is a pathogen.

14. A method of treating and preventing against fungal infections in a subject which comprises administering to the subject an effective amount of a compound having the structure:

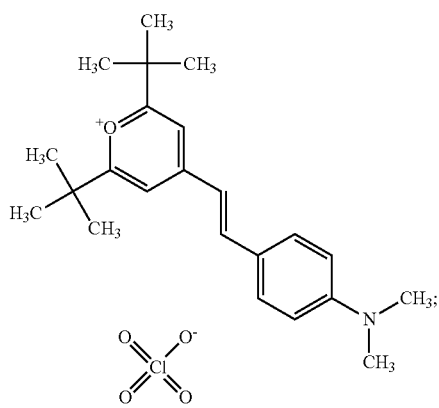 [SMILES: CN(C)c1ccc(/C=C/c2cc(C(C)(C)C)[o+]c(C(C)(C)C)c2)cc1 ; [O-][Cl+3]([O-])([O-])[O-]]

and a pharmaceutically acceptable carrier, wherein the fungal infection is caused by at least one species of the *Candida* genus.

15. The method of claim 14, wherein the fungal cell is a pathogen.

16. The method of claim 14, wherein the subject is a human.

17. The method of claim 16, wherein the subject is immunocompromised.

18. The method of claim 16, wherein the subject had received chemotherapy.

19. The method of claim 16, wherein the subject has AIDS.

20. The method of claim 16, wherein the subject had received a transplant.

21. The method of claim 16, wherein the subject has a central venous catheter.

22. The method of claim 16, wherein the compound is administered via injection, topical route, oral route, nasal route, aerosol, or enema route.

* * * * *